US007939674B2

(12) United States Patent
Wang et al.

(10) Patent No.: US 7,939,674 B2
(45) Date of Patent: *May 10, 2011

(54) PROCESS FOR PRODUCING AN AROMATIC UNSATURATED COMPOUND

(75) Inventors: Weiqi Wang, Ibaraki (JP); Tetsuya Ikemoto, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/346,494

(22) Filed: Dec. 30, 2008

(65) Prior Publication Data

US 2009/0111999 A1    Apr. 30, 2009

Related U.S. Application Data

(62) Division of application No. 10/569,486, filed as application No. PCT/JP2004/012601 on Aug. 25, 2004.

(30) Foreign Application Priority Data

Aug. 27, 2003  (JP) ................................. 2003-209042
Nov. 14, 2003  (JP) ................................. 2003-384566

(51) Int. Cl.
*C07D 209/18* (2006.01)
*C07C 67/00* (2006.01)
(52) U.S. Cl. ........................................ 548/494; 560/104
(58) Field of Classification Search .................. 548/469, 548/510; 514/415; 560/104
See application file for complete search history.

(56) References Cited

U.S. PATENT DOCUMENTS

| 5,118,853 A | 6/1992 | Lee et al. |
| 6,054,607 A | 4/2000 | Okui et al. |
| 7,700,642 B2 * | 4/2010 | Wang et al. ................... 514/415 |
| 2003/0166946 A1 | 9/2003 | Wolleb et al. |
| 2004/0176614 A1 | 9/2004 | Wolleb et al. |

FOREIGN PATENT DOCUMENTS

| JP | 45-37523 B1 | 11/1970 |
| JP | 6-72957 A | 3/1994 |
| JP | 10-212265 A | 8/1998 |
| JP | 11-217356 A | 8/1999 |
| JP | 2001-81057 A | 3/2001 |
| JP | 2004-75576 A | 3/2004 |
| WO | WO-01/92223 A1 | 12/2001 |
| WO | WO-03/024958 A2 | 3/2003 |

OTHER PUBLICATIONS

T. Yokota et al., J.Am. Chem.Soc., vol. 125, (2003), pp. 1476-1477.
H. Weissman et al., J.Am.Chem.Soc., vol. 123, (2001), pp. 337-338.
Y. Fujiwara et al., J.Org.Chem., vol. 46, (1981), pp. 851-855.
Y. Murakami et al., Heterocycles, vol. 22, No. 7, (1984), pp. 1493-1496.
T. Itahara et al., Synthesis, (1984), pp. 236-237.
D. G. Crosby et al., J.Org.Chem., vol. 27,(1962), pp. 3083-3085.
D. Crosby, J.Org.Chem., vol. 26, (1961), pp. 1215-1217.
T. Ziegler et al., Chem.Ber., vol. 120, (1987), pp. 373-378.
Gorbunova et al., "The interaction of 4-ethoxy-1, 1, 1-trifluoro-3-buten-2-one with C-nucleophiles—organo-magnesium and -zinc compounds", Journal of Fluorine Chemistry; vol, 65, pp. 25-28, 1993, XP 000601406.
Black et al, "Substitution, Oxidation and Addition Reactions at C-7 of Activated Indoles", Tetrahedron; vol. 50, No. 35, pp. 10497-10508, 1994, Pergamon.
Supplementary European Search Report issued on Jun. 20, 2007 in corresponding European Patent Application No. 04 77 2557.
European Patent Office Action issued on May 29, 2009 in corresponding European Patent Application No. 04 772 557.

* cited by examiner

*Primary Examiner* — Kamal A Saeed
*Assistant Examiner* — Kristin Bianchi
(74) *Attorney, Agent, or Firm* — Birch, Stewart, Kolasch & Birch, LLP

(57) ABSTRACT

The present invention provides a process for producing an aromatic unsaturated compound of the formula (4)

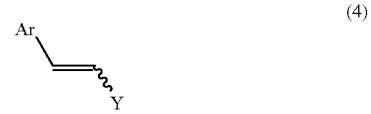

(4)

wherein Ar represents an optionally substituted aromatic group or an optionally substituted heteroaromatic group, and Y represents an electron withdrawing group,
which comprises reacting
(a) a compound of the formula (1)

Ar—H    (1)

wherein Ar has the same meaning as defined above
with
(b) a compound of the formula (2)

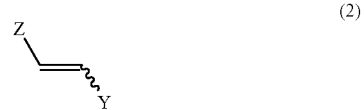

(2)

wherein Y has the same meaning as defined above, and Z represents a lower alkoxy, or
a compound of the formula (3)

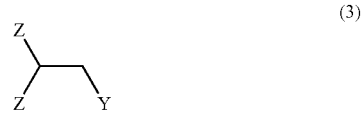

(3)

wherein Y and Z have the same meanings as defined above, in the presence of
(c) an acid or a compound which generates a mineral acid by its hydrolysis.

5 Claims, No Drawings

PROCESS FOR PRODUCING AN AROMATIC UNSATURATED COMPOUND

This application is a Divisional of co-pending application Ser. No. 10/569,486 filed on Feb. 24, 2006 and for which priority is claimed under 35 U.S.C. §120. application Ser. No. 10/569,486 is the national phase of PCT International Application No. PCT/JP2004/012601 filed on Aug. 25, 2004 under 35 U.S.C. §371. The entire contents of each of the above-identified applications are hereby incorporated by reference.

TECHNOLOGICAL FIELD

The present invention relates to a process for producing an aromatic unsaturated compound.

BACKGROUND TECHNOLOGY

An aromatic unsaturated compound of the formula (4)

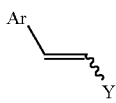

(4)

wherein Ar represents an optionally substituted aromatic group or an optionally substituted heteroaromatic group, and Y represents an electron withdrawing group (hereinafter, abbreviated as aromatic unsaturated compound (4)) is useful as, for example, a synthetic intermediate of medical and agricultural chemicals or the like. For example, a compound of the following formula (7)

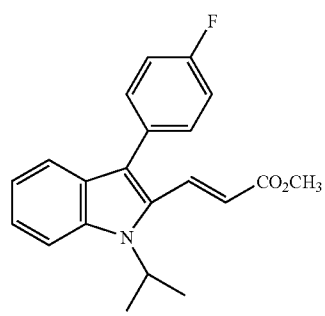

(7)

is known as a synthetic intermediate of fluvastatin useful as a hyperlipidemia drug as described also in, for example, WO 01/92223.

Compounds of the following formulae (8) and (9) are compounds being developed as an arteriosclerosis remedy as described also in JPH09-202775-A and JPH07-206842-A, respectively.

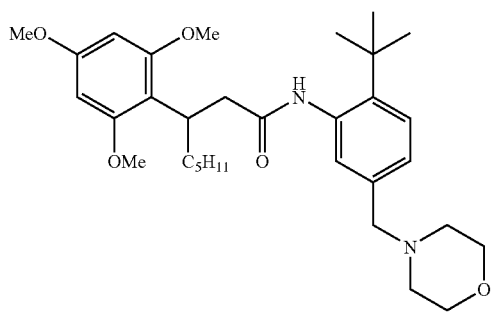

(8)

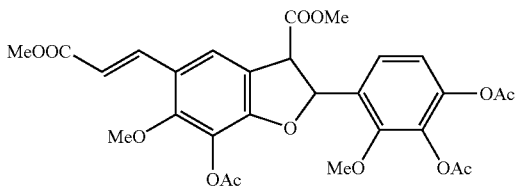

(9)

As a process for producing such an aromatic unsaturated compound (4), there is known, for example, a process reacting an aromatic halide with an acrylic acid compound such as acrylic acid and the like in the presence of a palladium catalyst and a base (for example, WO 01/92223), however, an aromatic halide manifesting high load on environments is required to be used as a raw material, and additionally, a hydrogen halide is by-produced together with progress of the reaction. In addition, since the above-mentioned hydrogen halide is required to be neutralized with a base, it is not necessarily a reaction of high atom economy from the standpoint of raw material.

On the other hand, as a process of higher atom economy, there is a process using a compound of the formula (1)

 Ar—H (1)

wherein, Ar is as defined above,
as a raw material and reacting it with an acrylic acid compound. For example, there are suggested (a) a process using a ruthenium catalyst and a palladium catalyst and reacting in the presence of oxygen (for example, J. Am. Chem. Soc., 125, 1467 (2003), J. Am. Chem. Soc., 123, 337 (2001)), (b) a process using a palladium complex in an amount equal to or more than the theoretical amount (for example, J. Org. Chem., 46, 851 (1981), Heterocycles, 22, 1493 (1984)), and the like.

However, the process (a) is not necessarily advantageous from the standpoint of operation and equipments since oxygen is used and accordingly the process is required to be performed under the reaction condition not higher than the explosion limit. The process (b) is disadvantageous from the standpoint of cost since a palladium complex in an amount equal to or more than the theoretical amount is used though it is a method of higher atom economy from the standpoint of raw material. In addition, post treatment of the palladium complex after the reaction is troublesome, further, the yield is low. That is, it is not necessarily an advantageous method from the standpoint of industrial production.

As a process for producing a compound having an indole ring, there is known a process protecting a nitrogen atom constituting an indole ring with a benzenesulfonyl group, then, reacting it with an acrylic acid compound in the presence of a palladium catalyst (for example, Synthesis, 236 (1984)). This process, however, is a reaction limited to a compound in which a nitrogen atom constituting an indole ring is protected with a benzenesulfonyl group, and additionally, needs a use in excess amount of a relatively expensive re-oxidizer such as, for example, silver acetate and the like for obtaining an intended object in good yield.

SUMMARY OF THE INVENTION

Under such conditions, the present inventors have intensively studied for developing a process for producing the above-mentioned aromatic unsaturated compound (4) with higher atom economy and more advantageously from industrial standpoint using a compound of the above-mentioned formula (1) as a raw material and resultantly found that the object of the instant application can be attained by reacting a compound of the above-mentioned formula (1) with a compound of the formula (2)

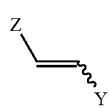

(2)

wherein Y represents an electron withdrawing group, and Z represents a lower alkoxy group,
or with a compound of the formula (3)

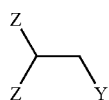

(3)

wherein, Y and Z have the same meanings as defined above, in the presence of an acid such as hydrochloric acid and the like, or a compound capable of generating a mineral acid by its hydrolysis such as phosphorus oxychloride and the like, leading to completion of the present invention.

That is, the present invention includes the following inventions.

<1> A process for producing an aromatic unsaturated compound of the formula (4) which comprises reacting (a) a compound of the formula (1) with (b) a compound of the formula (2) or a compound of the formula (3) in the presence of (c) an acid or a compound which generates a mineral acid by its hydrolysis.
<2> The process according to <1>, wherein the reaction is conducted in the co-presence of water.
<3> The process according to <1> or <2>, wherein (c) an acid or a compound which generates a mineral acid by its hydrolysis is hydrogen halide.
<4> The process according to <1> or <2>, wherein (c) an acid or a compound which generates a mineral acid by its hydrolysis is phosphorus oxyhalide, phosphorus halide, thionyl halide or sulfuryl halide.
<5> The process according to any of <1> to <4>, wherein the reaction is conducted in acetic acid.
<6> The process according to any of <1> to <5>, wherein Ar in the formulae (1) and (4) is an aromatic group or a heteroaromatic group which may be substituted by at least one group selected from the group consisting of a lower alkyl, a lower alkoxyl, a hydroxyl, —$OR^x$, an amino, —$NHR^y$, —$NR^y_2$, halogen and a phenyl optionally substituted by halogen(s),
wherein $R^x$ represents a protective group of hydroxyl and $R^y$ represents a protective group of amino.
<7> The process according to any of <1> to <6>, wherein Ar in the formulae (1) and (4) is an optionally substituted phenyl.
<8> The process according to any of <1> to <6>, wherein Ar in the formulae (1) and (4) is an optionally substituted indolyl.
<9> The process according to any of <1> to <6> or <8>, wherein the compound of the formula (1) is a compound of the formula (5)

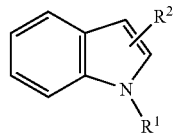

(5)

wherein $R^1$ represents a phenyl optionally substituted by halogen(s), a hydrogen or an alkyl and $R^2$ represents an alkyl or a phenyl optionally substituted by halogen(s), and
the compound of the formula (4) is a compound of the formula (6)

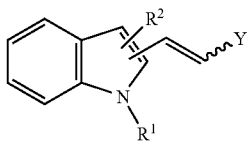

(6)

wherein $R^1$ and $R^2$ have the same meanings as defined above.

BEST MODES FOR CARRYING OUT THE INVENTION

In the formula of a compound of the formula (1)

Ar—H (1)

hereinafter abbreviated as compound (1), Ar represents an optionally substituted aromatic group or an optionally substituted heteroaromatic group.

Examples of the aromatic group include phenyl, naphthyl, anthryl, phenanthryl, tetrahydronaphthyl, 9,10-dihydroanthryl, acenaphthenyl and the like. Examples of the heteroaromatic group include aromatic groups containing hetero atom(s) such as a nitrogen atom, oxygen atom, sulfur atom and the like as constituent atom(s) of an aromatic ring, and specific examples thereof include indolyl, benzofuryl, benzothienyl, benzothiazolyl, benzooxazolyl, pyrrolyl, furyl, thienyldibenzofuryl, dibenzothienyl, 2,3-dihydroindolyl, 2,3-dihydrobenzofuryl and the like. Indolyl group is preferred as the heteroaromatic group.

Such aromatic groups or heteroaromatic groups may be substituted with substituent(s), and examples of the substituent include alkyls, usually, alkyls having 1 to 6 carbon atoms such as methyl, ethyl, n-propyl, isopropyl, n-butyl, isobutyl, sec-butyl, tert-butyl, n-pentyl, isopentyl, n-hexyl and the like, preferably, lower alkyls having 1 to 4 carbon atoms; lower alkoxys usually having 1 to 4 carbon atoms such as methoxy, ethoxy, n-propoxy, isopropoxy, n-butoxy, isobutoxy, sec-butoxy, tert-butoxy and the like; hydroxyl group; hydroxyl groups protected with a protective group represented by —$OR^x$; aminos; aminos protected with a protective group represented by —$NHR^y$ or —$NR^y_2$; halogens such as fluorine, chlorine, bromine, iodine and the like; phenyls optionally substituted with a halogen such as phenyl, 4-chlorophenyl, 4-fluorophenyl, and the like. Examples of the protective group on a hydroxyl group represented by $R^x$ include alkanoyls such as acetyl and the like; alkoxyalkyls such as methoxymethyl and the like; aralkyls such as benzyl and the like; alkylenes such as methylene, dimethylmethylene and the like, and examples of hydroxyl groups protected with such a protective group represented by —$OR^x$ include acetyloxy, methoxymethoxy, benzyloxy, methylenedioxy, dimethylmethylenedioxy and the like. Examples of the protective group on amino represented by $R^y$ include the above-mentioned alkanoyls; aralkyls such as benzyl and the like; aralkyloxyalkyls such as benzyloxymethyl and the like; dialkoxyalkyls such as dimethoxymethyl and the like; sulfonyls such as benzenesulfonyl, p-toluenesulfonyl, methanesulfonyl and the like, and examples of aminos protected with such a protective group represented by —$NHR^y$ or —$NR^y_2$ include acetylamino, dibenzylamino, dibenzyloxymethylamino, dimethoxymethylamino, benzenesulfonylamino, p-toluenesulfonylamino, methanesulfonyl amino and the like.

In the case of aromatic groups substituted with such a substituent, the number of such substituents is not particularly limited, however, aromatic groups substituted with two or more electron donating substituents are preferable, and aromatic groups substituted with three or more electron donating substituents are more preferable, from the standpoint of reaction speed. Also in the case of heteroaromatic groups substituted with a substituent, the number of such substituents is not particularly limited, however, heteroaromatic groups substituted with at least one electron donating substituents are preferable, from the standpoint of reaction speed. The electron donating substituent herein referred to indicates an alkyl, lower alkoxy having 1 to 4 carbon atoms, hydroxyl group, hydroxyl group protected with a protective group represented by —OR$^x$, amino, or amino protected with a protective group represented by —NHR$^y$ or —NR$^y_2$, among the above-mentioned substituents.

Among such compounds (1), compounds in which the heteroaromatic group is an indolyl group are important since they are synthetic raw materials of indole compounds such as, for example, fluvastatin and the like useful as a hyperlipidemia drug (e.g., JPH02-46031-B, WO01/92223, and the like), and examples of such compounds in which the heteroaromatic group is an indolyl group include compounds of the formula (5)

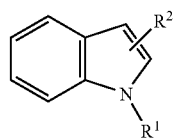

(5)

wherein, R$^1$ represents a phenyl optionally substituted with halogen(s), or represents hydrogen or alkyl, and R$^2$ represents an alkyl, or represents a phenyl optionally substituted with halogen(s).

In the above-mentioned formula (5), the phenyl optionally substituted with halogen(s) includes the same moieties as described above, and examples of the alkyl include alkyls having 1 to 6 carbon atoms such as methyl, ethyl, n-propyl, isopropyl, n-butyl, isobutyl, sec-butyl, tert-butyl, n-hexyl and the like.

Examples of such compounds (1) include benzene, naphthalene, dimethoxybenzene, 1,3,5-trimethoxybenzene, 1,2,3-trimethoxybenzene, 2,6-dimethoxyphenol, 2-methoxyaniline, 4-methoxyaniline, 2-methoxyacetanilide, 4-methoxyacetanilide, 2-acetylaminophenol, 4-acetylaminophenol, catechol, resorcinol, hydroquinone, 4-tert-butylcatechol, capsaicin, 2-methyl-1,4-indole, 2-methyl-1-methyl-1H-indole, 2-methyl-1-isopropyl-1H-indole, 2-methyl-1-phenyl-1H-indole, 2-ethyl-1H-indole, 2-ethyl-1-methyl-1H-indole, 2-ethyl-1-phenyl-1H-indole, 2-phenyl-1H-indole, 2-phenyl-1-methyl-1H-indole, 2-phenyl-1-phenyl-1H-indole, 3-methyl-1H-indole, 3-methyl-1-methyl-1H-indole, 3-methyl-1-isopropyl-1H-indole, 3-methyl-1-phenyl-1H-indole, 3-ethyl-1H-indole, 3-ethyl-1-methyl-1H-indole, 3-ethyl-1-phenyl-1H-indole, 3-phenyl-1H-indole, 3-phenyl-1-methyl-1H-indole, 3-phenyl-1-phenyl-1H-indole, 3-(4-fluorophenyl)-1-isopropyl-1H-indole, and the like.

As such compounds (1), commercially available compounds may be used, and those produced according to known methods may also be used. For example, a compound in which the aromatic group is an indolyl group can be produced according to known methods such as, for example, Tetrahedron Letters, 26, 2155 (1985) and the like.

In a compound of the formula (2)

(2)

hereinafter abbreviated as compound (2), and a compound of the formula (3)

(3)

hereinafter abbreviated as compound (3), Y represents an electron withdrawing group, and Z represents a lower alkoxy.

Examples of the electron withdrawing group include alkoxycarbonyl, aryloxycarbonyl, aralkyloxycarbonyl, acyl, cyano and the like. Examples of the alkoxycarbony include alkoxycarbonyls having 2 to 9 carbon atoms such as methoxycarbonyl, ethoxycarbonyl, n-propoxycarbonyl, isopropoxycarbonyl, n-butoxycarbonyl, isobutoxycarbonyl, tert-butoxycarbonyl, n-hexyloxycarbonyl, n-octyloxycarbonyloxy and the like. Examples of the aryloxycarbonyl include aryloxycarbonyls having 7 to 13 carbon atoms such as phenoxycarbonyl, and the like, and examples of the aralkyloxycarbonyl include aralkyloxycarbonyls having 8 to 14 carbon atoms such as benzyloxycarbonyl, and the like. Examples of the acyl include aliphatic acyls having 2 to 9 carbon atoms such as acetyl, propionyl and the like; aromatic acyls having 7 to 13 carbon atoms such as benzoyl, and the like. Examples of the lower alkoxy include alkoxys having 1 to 6 carbon atoms such as methoxy, ethoxy, n-propoxy, isopropoxy, n-butoxy, isobutoxy, sec-butoxy, tert-butoxy, n-pentyloxy, n-hexyloxy and the like, and preferable are alkoxys having 1 to 4 carbon atoms.

Examples of such compounds (2) include methyl 3-methoxyacrylate, ethyl 3-methoxyacrylate, n-propyl 3-methoxyacrylate, isopropyl 3-methoxyacrylate, n-butyl 3-methoxyacrylate, isobutyl 3-methoxyacrylate, sec-butyl 3-methoxyacrylate, tert-butyl 3-methoxyacrylate, phenyl 3-methoxyacrylate, benzyl 3-methoxyacrylate, methyl 3-ethoxyacrylate, ethyl 3-ethoxyacrylate, n-propyl 3-ethoxyacrylate, isopropyl 3-ethoxyacrylate, n-butyl 3-ethoxyacrylate, isobutyl 3-ethoxyacrylate, sec-butyl 3-ethoxyacrylate, tert-butyl 3-ethoxyacrylate, phenyl 3-ethoxyacrylate, benzyl 3-ethoxyacrylate, methyl 3-isopropoxyacrylate, ethyl 3-isopropoxyacrylate, n-propyl 3-isopropoxyacrylate, isopropyl 3-isopropoxyacrylate, n-butyl 3-isopropoxyacrylate, isobutyl 3-isopropoxyacrylate, sec-butyl 3-isopropoxyacrylate, tert-butyl 3-isopropoxyacrylate, phenyl 3-isopropoxyacrylate, benzyl 3-isopropoxyacrylate, methyl 3-n-butoxyacrylate, ethyl 3-n-butoxyacrylate, n-propyl 3-n-butoxyacrylate, isopropyl 3-n-butoxyacrylate, n-butyl 3-n-butoxyacrylate, isobutyl 3-n-butoxyacrylate, sec-butyl 3-n-butoxyacrylate, tert-butyl 3-n-butoxyacrylate, phenyl 3-n-butoxyacrylate, benzyl 3-n-butoxyacrylate, methyl 3-tert-butoxyacrylate, ethyl 3-tert-butoxyacrylate, n-propyl 3-tert-butoxyacrylate, isopropyl 3-tert-butoxyacrylate, n-butyl 3-tert-butoxyacrylate, isobutyl 3-n-butoxyacrylate, sec-butyl 3-tert-butoxyacrylate, tert-butyl 3-tert-butoxyacrylate, phenyl 3-tert-butoxyacrylate, benzyl 3-tert-butoxyacrylate, 3-methoxyacrylonitrile, 3-ethoxyacrylonitrile, 3-isopropoxyacrylonitrile, 3-n-butoxyacrylonitrile, 3-tert-butoxyacrylonitrile, 4-methoxy-3-buten-2-one, 4-ethoxy-3-buten-2-one, 3-methoxy-1-phenylpropenone and the like.

In the compound (2), a trans isomer and cis isomer exists, and any one of them may be used or any mixture of them may be used in the present invention.

Examples of the compound (3) include methyl 3,3-dimethoxypropionate, ethyl 3,3-dimethoxypropionate, n-propyl 3,3-dimethoxypropionate, isopropyl 3,3-dimethoxypropionate, n-butyl 3,3-dimethoxypropionate, isobutyl 3,3-dimethoxypropionate, sec-butyl 3,3-dimethoxypropionate, tert-butyl 3,3-dimethoxypropionate, phenyl 3,3-dimethoxypropionate, benzyl 3,3-dimethoxypropionate, methyl 3,3-diethoxypropionate, ethyl 3,3-diethoxypropionate, n-propyl 3,3-diethoxypropionate, isopropyl 3,3-diethoxypropionate, n-butyl 3,3-diethoxypropionate, isobutyl 3,3-diethoxypropionate, sec-butyl 3,3-diethoxypropionate, tert-butyl 3,3-diethoxypropionate, phenyl 3,3-diethoxypropionate, benzyl 3,3-diethoxypropionate, methyl 3,3-diisopropoxypropionate, ethyl 3,3-diisopropoxypropionate, n-propyl 3,3-diisopropoxypropionate, isopropyl 3,3-diisopropoxypropionate, n-butyl 3,3-diisopropoxypropionate, isobutyl 3,3-diisopropoxypropionate, sec-butyl 3,3-diisopropoxypropionate, tert-butyl 3,3-diisopropoxypropionate, phenyl 3,3-diisopropoxypropionate, benzyl 3,3-diisopropoxypropionate, methyl 3,3-di(n-butoxy)propionate, ethyl 3,3-di(n-butoxy)propionate, n-propyl 3,3-di(n-butoxy)propionate, isopropyl 3,3-di(n-butoxy)propionate, n-butyl 3,3-di(n-butoxy)propionate, isobutyl 3,3-di(n-butoxy)propionate, sec-butyl 3,3-di(n-butoxy)propionate, tert-butyl 3,3-di(n-butoxy)propionate, phenyl 3,3-di(n-butoxy)propionate, benzyl 3,3-di(n-butoxy)propionate, methyl 3,3-di(tert-butoxy)propionate, ethyl 3,3-di(tert-butoxy)propionate, n-propyl 3,3-di(tert-butoxy)propionate, isopropyl 3,3-di(tert-butoxy)propionate, n-butyl 3,3-di(tert-butoxy)propionate, isobutyl 3,3-di(tert-butoxy)propionate, sec-butyl 3,3-di(tert-butoxy)propionate, tert-butyl 3,3-di(tert-butoxy)propionate, phenyl 3,3-di(tert-butoxy)propionate, benzyl 3,3-di(tert-butoxy)propionate, 3,3-dimethoxypropionitrile, 3,3-diethoxypropionitrile, 3,3-diisopropoxypropionitrile, 3,3-di(n-butoxy)propionitrile, 3,3-di(tert-butoxy)propionitrile, 1,1-dimethoxy-3-butanone, 1,1-diethoxy-3-butanone, 3,3-dimethoxy-1-phenylpropan-1-one, and the like.

As such compounds (2) and compounds (3), commercially available compounds may be used, and those produced according to known method, such as JPS61-45974-B, JPS58-26855-A and the like may also be used.

The amount used of the compound (2) or compound (3) is usually 1 to 5 mol, preferably 1 to 3 mol in total based on 1 mol of the compound (1).

Examples of the acid include sulfuric acid; hydrochloric acid; hydrogen halides such as hydrogen bromide and the like; perhalogenic acids such as perchloric acid; sulfonic acids such as methanesulfonic acid, benzenesulfonic acid, p-toluenesulfonic acid, trifluoromethanesulfonic acid and the like; perfluorocarboxylic acids such as trifluoroacetic acid and the like; aprotic acids such as boron trifluoride, aluminum chloride, aluminum bromide, zinc chloride, zinc bromide, tin chloride, titanium tetrachloride and the like; acidic ion exchange resins and the like, and preferable are hydrogen halides. As the aprotic acid, complexes of aprotic acids such as, for example, a boron trifluoride-tetrahydrofuran complex and the like may also be used. In the method of the present invention, when the acid to be used is a protonic acid, acids having a pKa of 2.5 or less are preferred, and acids having a pKa of 1.5 or less are more preferred.

Examples of the compound capable of generating a mineral acid by hydrolysis (hereinafter, may be referred to as MAGH compound) include phosphorus oxyhalides such as phosphorus oxychloride, phosphorus oxybromide and the like; phosphorus halides such as phosphorus trichloride, phosphorus tribromide, phosphorus pentachloride and the like; thionyl halides such as thionyl chloride and the like; sulfuryl halides such as sulfuryl chloride, and the like, and preferable are phosphorus oxyhalides.

A compound (1) may be reacted with a compound (2) or a compound (3) in the presence of an acid, or a compound (1) may be reacted with a compound (2) or a compound (3) in the presence of a MAGH compound. Alternatively, a compound (1) may also be reacted with a compound (2) or a compound (3) in the presence of an acid and MAGH compound.

The mixing order of them is not particularly limited, and for example, an acid or MAGH compound may be added to a mixture of a compound (1) and a compound (2) or a compound (3), or a compound (2) or a compound (3) may be added to a mixture of a compound (1) and an acid or MAGH compound.

The amount used of an acid or MAGH compound is usually 0.001 mol or more, preferably 0.01 mol or more in total based on 1 mol of the compound (1), the upper limit thereof is not particularly set, and in the case of liquid under reaction conditions, it may be used in excess amount for acting also as a solvent, and the amount is practically 5 mol or less, preferably 3 mol or less from the standpoint of post treatment and economy.

The reaction is performed usually in the presence of a solvent, and examples of the solvent include nitrile-based solvents such as acetonitrile, propionitrile and the like, carboxylic acid-based solvents such as formic acid, acetic acid and the like, halogenated hydrocarbon-based solvents such as dichloromethane, chloroform and the like, ether-based solvents such as tetrahydrofuran and the like, ester-based solvents such as ethyl acetate and the like, alcohol-based solvents such as methanol, ethanol, isopropanol and the like, water, and the like, which may be single solvent or mixed solvent, and preferable are carboxylic acid-based solvents and nitrile-based solvents, and more preferable are carboxylic acid-based solvents, and among them, acetic acid is particularly preferable. The amount used of such solvents is not particularly limited. As described above, when the abovementioned acid or MAGH compound is liquid under reaction conditions, such an acid or MAGH compound may be used as a solvent.

The intended aromatic unsaturated compound (4) can be obtained by reacting a compound (1) with a compound (2) or compound (3) in the presence of an acid or MAGH compound. The aromatic unsaturated compound (4) can be obtained with better yield by carrying out the reaction in the coexistence of water.

The amount used of water when the reaction is carried out in the coexistence of water is usually 0.1 mol or more based on 1 mol of the compound (1), and though its upper limit is not particularly limited, it is practically 50 mol or less, preferably 10 mol or less.

The reaction temperature is usually −20 to 80° C.

After completion of the reaction, the intended aromatic unsaturated compound (4) can be taken out by, for example, filtration treatment, after mixing the reaction liquid with water. In a certain case, the aromatic unsaturated compound (4) precipitates as crystals in the reaction liquid. In such a case, the aromatic unsaturated compound (4), may be taken out directly by filtration treatment of the reaction liquid, or by filtration treatment after mixing the reaction liquid and water. Alternatively, the compound (4) may also be taken out, for example, by adding water and water-insoluble organic solvent such as toluene, ethyl acetate, methyl t-butyl ether, methyl isobutyl ketone and the like to the reaction liquid, extracting the mixture, and concentrating the resulting organic layer. The obtained aromatic unsaturated compound (4) may further be purified by conventional purification means such as, for example, recrystallization, column chromatography and the like.

Examples of thus obtained aromatic unsaturated compound (4) include methyl 3-(2,4,6-trimethoxyphenyl)acrylate, methyl 3-(2,3,4-trimethoxyphenyl)acrylate, methyl 3-(3-hydroxy-2,4-dimethoxyphenyl)acrylate, methyl 3-(3,4-dihydroxyphenyl)acrylate, ethyl 3-(2,4,6-trimethoxyphenyl)acrylate, ethyl 3-(2,3,4-trimethoxyphenyl)acrylate, ethyl 3-(3-hydroxy-2,4-dimethoxyphenyl)acrylate, ethyl 3-(3,4-dihydroxyphenyl)acrylate, n-propyl 3-(2,4,6-trimethoxyphenyl)acrylate, n-propyl 3-(2,3,4-trimethoxyphenyl)acrylate, n-propyl 3-(3-hydroxy-2,4-dimethoxyphenyl)acrylate, n-propyl 3-(3,4-dihydroxyphenyl)acrylate, isopropyl 3-(2,4,6-trimethoxyphenyl)acrylate, isopropyl 3-(2,3,4-trimethoxyphenyl)acrylate, isopropyl 3-(3-hydroxy-2,4-dimethoxyphenyl)acrylate, isopropyl 3-(3,4-dihydroxyphenyl)acrylate, n-butyl 3-(2,4,6-trimethoxyphenyl)acrylate, n-butyl 3-(2,3,4-trimethoxyphenyl)acrylate, n-butyl 3-(3-hydroxy-2,4-dimethoxyphenyl)acrylate, n-butyl 3-(3,4-dihydroxyphenyl)acrylate, isobutyl 3-(2,4,6-trimethoxyphenyl)acrylate, isobutyl 3-(2,3,4-trimethoxyphenyl)acrylate, isobutyl 3-(3-hydroxy-2,4-dimethoxyphenyl)acrylate, isobutyl 3-(3,4-dihydroxyphenyl)acrylate, phenyl 3-(2,4,6-trimethoxyphenyl)acrylate, phenyl 3-(2,3,4-trimethoxyphenyl)acrylate, phenyl 3-(3-hydroxy-2,4-dimethoxyphenyl)acrylate, phenyl 3-(3,4-dihydroxyphenyl)acrylate, benzyl 3-(2,4,6-trimethoxyphenyl)acrylate, benzyl 3-(2,3,4-trimethoxyphenyl)acrylate, benzyl 3-(3-hydroxy-2,4-dimethoxyphenyl)acrylate, benzyl 3-(3,4-dihydroxyphenyl)acrylate, 3-(2,4,6-trimethoxyphenyl)acrylonitrile, 3-(2,3,4-trimethoxyphenyl)acrylonitrile, 3-(3-hydroxy-2,4-dimethoxyphenyl)acrylonitrile, 3-(3,4-dihydroxyphenyl)acrylonitrile, 4-(2,4,6-trimethoxyphenyl)-3-buten-2-one, 4-(2,3,4-trimethoxyphenyl)-3-buten-2-one, 4-(3-hydroxy-2,4-dimethoxyphenyl)-3-buten-2-one, 4-(3,4-dihydroxyphenyl)-3-buten-2-one, 3-(2,3,4-trimethoxyphenyl)-1-phenylpropenone, 3-(3-hydroxy-2,4-dimethoxyphenyl)-1-phenylpropenone, 3-(3,4-dihydroxyphenyl)-1-phenylpropenone, methyl 3-[3-(4-fluorophenyl)-1-isopropyl-1H-indol-2-yl]acrylate, ethyl 3-[3-(4-fluorophenyl)-1-isopropyl-1H-indol-2-yl]acrylate, n-propyl 3-[3-(4-fluorophenyl)-1-isopropyl-1H-indol-2-yl]acrylate, isopropyl 3-[3-(4-fluorophenyl)-1-isopropyl-1H-indol-2-yl]acrylate, n-butyl 3-[3-(4-fluorophenyl)-1-isopropyl-1H-indol-2-yl]acrylate, isobutyl 3-[3-(4-fluorophenyl)-1-isopropyl-1H-indol-2-yl]acrylate, tert-butyl 3-[3-(4-fluorophenyl)-1-isopropyl-1H-indol-2-yl]acrylate, phenyl 3-[3-(4-fluorophenyl)-1-isopropyl-1H-indol-2-yl]acrylate, benzyl 3-[3-(4-fluorophenyl)-1-isopropyl-1H-indol-2-yl]acrylate, 3-[3-(4-fluorophenyl)-1-isopropyl-1H-indol-2-yl]acrylonitrile, methyl 3-(1-methyl-2-phenyl-1-indol-3-yl)acrylate, ethyl 3-(1-methyl-2-phenyl-1H-indol-3-yl)acrylate, n-propyl 3-(1-methyl-2-phenyl-1H-indol-3-yl)acrylate, isopropyl 3-(1-methyl-2-phenyl-1H-indol-3-yl)acrylate, n-butyl 3-(1-methyl-2-phenyl-1H-indol-3-yl)acrylate, isobutyl 3-(1-methyl-2-phenyl-1H-indol-3-yl)acrylate, tert-butyl 3-(1-methyl-2-phenyl-1H-indol-3-yl)acrylate, phenyl 3-(1-methyl-2-phenyl-1H-indol-3-yl)acrylate, benzyl 3-(1-methyl-2-phenyl-1H-indol-3-yl)acrylate, 3-(1-methyl-2-phenyl-1H-indol-3-yl)acrylonitrile, 4-[3-(4-fluorophenyl)-1-isopropyl-1H-indol-2-yl]-3-buten-2-one, 4-(1-methyl-2-phenyl-1H-indol-3-yl)-3-buten-2-one, 3-[3-(4-fluorophenyl)-1-isopropyl-1H-indol-2-yl]-1-phenylpropenone, 3-(1-methyl-2-phenyl-1H-indol-3-yl)-1-phenylpropenone, and the like.

In this reaction, both when a trans isomer is used and when a cis isomer is used as the compound (2), there are usually obtained a trans isomer of an aromatic unsaturated compound (4) or a trans-cis isomer mixture of an aromatic unsaturated compound (4) containing mainly a trans isomer.

Of such aromatic unsaturated compounds (4), compounds having a 3-(4-fluorophenyl)indolyl group in its molecule represented by, for example, the following formula (7) and the like can be converted into fluvastatin useful as a hyperlipidemia drug according to, for example, a method of WO 01/92223.

The present invention will be illustrated further in detail by the following examples, but the scope of the invention is not limited to these examples.

EXAMPLE 1

1.01 g of 3-(4-fluorophenyl)-1-isopropyl-1H-indole, 0.92 g of methyl 3,3-dimethoxypropionate, 0.72 mL of 90 wt % aqueous acetic acid (containing 4 mmol of water) and 6 mL of glacial acetic acid were mixed, then, 0.33 g of phosphorus oxychloride was added dropwise into the mixture at an inner temperature of 25° C., the added mixture was stirred for 9 hours at the same temperature to cause a reaction. After completion of the reaction, 16 mL of water was added dropwise into the reaction liquid, and the precipitated crystals were filtrated. The crystals were washed with 20 vol % aqueous methanol, then, dried to obtain 1.25 g of methyl trans-3-[3-(4-fluorophenyl)-1-isopropyl-1H-indol-2-yl]acrylate (yellow solid). Yield: 93%.

$^1$H-NMR (δ/ppm, CDCl$_3$, 400 MHz)

1.70 (6H, d, J=7 Hz), 3.76 (3H, s), 4.95 (1H, m), 5.96 (1H, d, J=16 Hz), 7.50 (1H, d, J=8 Hz), 7.57 (1H, d, J=8 Hz), 7.08 to 7.40 (6H, m), 7.82 (1H, d, J=16 Hz)

EXAMPLE 2

1.04 g of 1-methyl-2-phenyl-1H-indol, 0.64 g of methyl trans-3-methoxyacrylate, 94.5 mg of water and 6 ml of glacial acetic acid were mixed, 124 mg of phosphorus oxychloride was added into the mixture at an inner temperature of 25° C., the added mixture was stirred for 7 hours at the same temperature to cause a reaction. After completion of the reaction, 30 mL of water was added dropwise into the reaction liquid, 50 mL of ethyl acetate was added and extraction treatment was conducted, and the resulting organic layer was subjected to concentration treatment. The resultant concentrated residue was purified by flash chromatography, to obtain 1.11 g of methyl trans-3-(1-methyl-2-phenyl-1H-indol-3-yl)acrylate (yellow solid). Yield: 76%.

$^1$H-NMR (δ/ppm, CDCl$_3$, 400 MHz)

3.64 (3H, s), 3.74 (3H, s), 6.46 (1H, d, J=16 Hz), 7.29 to 7.55 (9H, m), 7.72 (1H, d, J=16 Hz)

EXAMPLE 3

1.68 g of 1,3,5-trimethoxybenzene, 2.32 g of methyl trans-3-methoxyacrylate, 0.18 g of water and 6 mL of glacial acetic acid were mixed, 164 mg of phosphorus oxychloride was added into the mixture at an inner temperature of 25° C., the added mixture was stirred for 3 hours at the same temperature to cause a reaction. After completion of the reaction, 36 mL of water was added dropwise into the reaction liquid, and the precipitated crystals were filtrated. The crystals were washed with 20 vol % of aqueous methanol, then, dried to obtain 2.28 g of methyl trans-3-(2,4,6-trimethoxyphenyl)acrylate (white solid). Yield: 91%.

$^1$H-NMR (δ/ppm, CDCl$_3$, 400 MHz)

3.79 (3H, s), 3.85 (3H, s), 3.87 (6H, s), 6.12 (2H, s), 6.76 (1H, d, J=16 Hz), 8.08 (1H, d, J=16 Hz)

EXAMPLE 4

1.7 g of 1,3,5-trimethoxybenzene, 1.68 g of methyl 3,3-dimethoxypropionate and 12 mL of glacial acetic acid were mixed, 313 mg of 35 wt % hydrochloric acid was added into the mixture at an inner temperature of 25° C., the added mixture was stirred for 1 hour at the same temperature to cause a reaction. After completion of the reaction, 36 mL of water was added dropwise into the reaction liquid, and the precipitated crystals were filtrated. The crystals were washed with 20 vol % of aqueous methanol, then, dried to obtain 2.46 g of methyl trans-3-(2,4,6-trimethoxyphenyl)acrylate (white solid). Yield: 98%.

EXAMPLE 5

1.68 g of 1,2,3-trimethoxybenzene, 1.34 g of methyl trans-3-methoxyacrylate and 6 mL of glacial acetic acid were mixed, 313 mg of 35 wt % hydrochloric acid was added into the mixture at an inner temperature of 25° C., the added mixture was stirred for 16 hours at the same temperature to cause a reaction. After completion of the reaction, 30 ml, of water and 50 mL of ethyl acetate were added into the reaction liquid, and extraction treatment was conducted. The resultant organic layer was washed with water, then, concentrated, and the resultant concentrated residue was purified by silica gel column chromatography (developing liquid: n-heptane/ethyl acetate=6/1 to 5/1), to obtain 0.63 g of methyl trans-3-(2,3,4-trimethoxyphenyl)acrylate (white solid). 0.92 g of the raw material 1,2,3-trimethoxybenzene was recovered. The yield of methyl 3-(2,3,4-trimethoxyphenyl)acrylate based on the converted 1,2,3-trimethoxybenzene was 55%.

$^1$H-NMR (δ/ppm, CDCl$_3$, 400 MHz)

3.80 (3H, s), 3.88 (3H, s), 3.89 (3H, s), 3.92 (3H, s), 6.42 (1H, d, J=16 Hz), 6.69 (1H, d, J=9 Hz), 7.26 (1H, d, J=9 Hz), 7.88 (1H, d, J=16 Hz)

EXAMPLE 6

The reaction and post treatment were conducted in the same manner as in Example 5 except that 1.54 g of 2,6-dimethoxyphenol was used instead of 1.68 g of 1,2,3-trimethoxybenzene, to obtain 0.76 g of methyl trans-3-(3-hydroxy-2,4-dimethoxyphenyl)acrylate (white solid). Yield: 32%.

$^1$H-NMR (δ/ppm, CDCl$_3$, 400 MHz)

3.80 (3H, s), 3.91 (3H, s), 3.93 (3H, s), 5.58 (1H, s), 6.45 (1H, d, J=16 Hz), 6.67 (1H, d, J=9 Hz), 7.07 (1H, d, J=9 Hz), 7.87 (1H, d, J=16 Hz)

EXAMPLE 7

Into a solution prepared by dissolving 0.63 g of 3-(4-fluorophenyl)-1-isopropyl-1H-indole in 3 mL of dichloromethane was added dropwise 0.77 g of phosphorus oxychloride at an inner temperature of 0 to 10° C., then, 0.92 g of trans-3-methoxyacrylonitrile was added dropwise. Then, the mixture was stirred overnight at room temperature to cause a reaction, further, the mixture was reacted for 6 hours at the reflux temperature. After completion of the reaction, the reaction liquid was added into 100 mL of 5 wt % aqueous sodium hydrogen carbonate, and extracted with ethyl acetate three times. The resulting organic layers were combined and washed with water, then, dried with anhydrous magnesium sulfate. The magnesium sulfate was filtrated off, and the resulting filtrate was concentrated to obtain a concentrated residue containing 3-[3-(4-fluorophenyl)-1-isopropyl-1H-indol-2-yl]acrylonitrile (trans-cis isomer mixture containing mainly trans isomer). The resulting concentrated residue was purified by silica gel column chromatography (developing liquid: n-heptane/ethyl acetate: 10/1 to 5/1) to obtain 0.34 g of trans-3-[3-(4-fluorophenyl)-1-isopropyl-1H-indol-2-yl] acrylonitrile (yellow solid). Yield: 45%

$^1$H-NMR (δ/ppm, CDCl$_3$, 400 MHz)

1.70 (6H, d, J=7 Hz), 4.85 (1H, m), 5.35 (1H, d, J=16 Hz), 7.09 to 7.46 (7H, m), 7.55 (1H, d, J=8 Hz), 7.48 (1H, d, J=16 Hz)

EXAMPLE 8

0.62 g of 3-(4-fluorophenyl)-1-isopropyl-1H-indole, 0.57 g of methyl trans-3-methoxyacrylate, 46 mg of water and 6.4 mL of glacial acetic acid were mixed, then, 66 mg of phosphorus oxychloride was added dropwise into the mixture at an inner temperature of 25° C., the added mixture was stirred for 21 hours at the same temperature to cause a reaction. After completion of the reaction, the same post treatment was conducted as in Example 1 to obtain 0.65 g of methyl trans-3-[3-(4-fluorophenyl)-1-isopropyl-1H-indol-2-yl]acrylate (yellow solid). Yield: 79%.

EXAMPLE 9

The reaction and post treatment were conducted in the same manner as in Example 8 except that the amount of phosphorus oxychloride was 164 mg and the reaction time was 9 hours, to obtain 0.79 g of methyl trans-3-[3-(4-fluorophenyl)-1-isopropyl-1H-indol-2-yl]acrylate (yellow solid). Yield: 96%.

EXAMPLES 10 TO 13

The reaction and post treatment were conducted in the same manner as in Example 8 except that acids shown in Table 1 were used instead of phosphorus oxychloride, the amount of glacial acetic acid was 6 mL and conditions shown in Table 1 were used, to obtain methyl trans-3-[3-(4-fluorophenyl)-1-isopropyl-1H-indol-2-yl]acrylate (yellow solid). The results are shown in Table 1.

TABLE 1

| Example | Acid (mg) | Water | Reaction time | Yield |
|---|---|---|---|---|
| 10 | 99 wt % sulfuric acid (156) | 46 mg | 15 Hr | 59% |
| 11 | 35 wt % hydrochloric acid (166) | 108 mg (water in hydrochloric acid) | 15 Hr | 94% |
| 12 | p-toluenesulfonic acid monohydrate (302) | 56 mg (containing 10 mg of crystal water) | 15 Hr | 74% |
| 13 | 47 wt % aqueous hydrobromic acid (274) | 145 mg water in aqueous hydrobromic acid | 5 Hr | 90% |

EXAMPLE 14

0.31 g of 3-(4-fluorophenyl)-1-isopropyl-1H-indole, 0.28 g of methyl trans-3-methoxyacrylate, 36 mg of water and 6 mL of acetonitrile were mixed, then, 164 mg of phosphorus oxychloride was added dropwise into the mixture at an inner temperature of 25° C., the added mixture was stirred for 22 hours at the same temperature to cause a reaction. After completion of the reaction, the same post treatment was conducted as in Example 1 to obtain 0.21 g of methyl trans-3-[3-(4-fluorophenyl)-1-isopropyl-1H-indol-2-yl]acrylate (yellow solid). Yield: 51%.

EXAMPLE 15

2.53 g of 3-(4-fluorophenyl)-1-isopropyl-1H-indole, 2.32 g of methyl trans-3-methoxyacrylate, 0.3 g of water and 15 mL of acetonitrile were mixed, then, 2.51 g of phosphorus oxychloride was added dropwise into the mixture at an inner temperature of 25° C., the added mixture was stirred for 19 hours at the same temperature to cause a reaction. After completion of the reaction, the same post treatment was conducted as in Example 1 to obtain 2.17 g of methyl trans-3-[3-(4-fluorophenyl)-1-isopropyl-1H-indol-2-yl]acrylate (yellow solid). Yield: 65%.

EXAMPLES 16 TO 18

The reaction and post treatment were conducted in the same manner as in Example 14 except that the use amounts of phosphorus oxychloride and water were as shown in Table 2 and the reaction time was 18 hours, to obtain methyl trans-3-[3-(4-fluorophenyl)-1-isopropyl-1H-indol-2-yl]acrylate (yellow solid). The results are shown in Table 2.

TABLE 2

| Example | Use amount of phosphorus oxychloride (mg) | Use amount of water (mg) | Yield |
| --- | --- | --- | --- |
| 16 | 242 | 44 | 56% |
| 17 | 398 | 44 | 75% |
| 18 | 348 | 0 | 32% |

EXAMPLES 19 TO 20

The reaction and post treatment were conducted in the same manner as in Example 14 except that acids shown in Table 3 were used instead of phosphorus oxychloride and the reaction time was 19 hours, to obtain methyl trans-3-[3-(4-fluorophenyl)-1-isopropyl-1H-indol-2-yl]acrylate (yellow solid). The results are shown in Table 3.

TABLE 3

| Example | Acid (mg) | Yield |
| --- | --- | --- |
| 19 | boron trifluoride•tetrahydrofuran complex (348) | 27% |
| 20 | 99 wt % sulfuric acid (119) | 39% |

EXAMPLE 21

1.27 g of 3-(4-fluorophenyl)-1-isopropyl-1H-indole, 1.16 g of methyl trans-3-methoxyacrylate and 12 mL of glacial acetic acid were mixed, then, 797 mg of 30 wt % hydrogen bromide/acetic acid solution was added dropwise into the mixture at an inner temperature of 25° C., the mixture was stirred for 5 hours at the same temperature to cause a reaction. After completion of the reaction, the same post treatment was conducted as in Example 1 to obtain 0.15 g of methyl trans-3-[3-(4-fluorophenyl)-1-isopropyl-1H-indol-2-yl]acrylate (yellow solid). Yield: 8%.

EXAMPLE 22

1.27 g of 3-(4-fluorophenyl)-1-isopropyl-1H-indole, 1.32 g of 1,1-dimethoxy-3-butanone and 6 mL of formic acid were mixed, then, 0.78 g of 30 wt % hydrogen bromide/acetic acid solution was added into the mixture at room temperature, the added mixture was stirred for 19 hours at the same temperature to cause a reaction. After completion of the reaction, 50 mL of ethyl acetate and 20 ml, of water were added and extraction treatment was conducted, the resulting organic layers were washed with water, then, dried with anhydrous magnesium sulfate. The magnesium sulfate was filtrated, then, the resulting filtrate was concentrated, to obtain a concentrated residue containing trans-4-[3-(4-fluorophenyl)-1-isopropyl-1H-indol-2-yl]-3-buten-2-one. The concentrated residue was purified by silica gel chromatography (developing liquid: n-heptane/ethyl acetate: 4/1) to obtain 0.72 g of trans-4-[3-(4-fluorophenyl)-1-isopropyl-1H-indol-2-yl]-3-buten-2-one (yellow solid). Yield: 52%. 0.18 g of the raw material 3-(4-fluorophenyl)-1-isopropyl-1H-indole were recovered together.

$^1$H-NMR (δ/ppm, CDCl$_3$, 400 MHz)

1.71 (6H, d, J=7 Hz), 2.23 (3H, s), 4.94 (1H, m), 6.29 (1H, d, J=16 Hz), 7.09 to 7.40 (6H, m), 7.49 (1H, J=8 Hz), 7.51 (1H, J=8 Hz), 7.66 (1H, d, J=16 Hz)

EXAMPLE 23

1.27 g of 3-(4-fluorophenyl)-1-isopropyl-1H-indole, 1.32 g of 1,1-dimethoxy-3-butanone and 6 mL of acetic acid were mixed, then, 260 mg of 35 wt % hydrochloric acid was added into the mixture at room temperature, the added mixture was stirred for 18 hours at the same temperature to cause a reaction. After completion of the reaction, two drops of the reaction liquid were sampled. The sampled liquid was concentrated under reduced pressure, and the resulting concentration residue was dissolved in chloroform-d, and $^1$H-NMR spectrum was measured to find that the above-mentioned concentrated residue contained trans-4-[3-(4-fluorophenyl)-1-isopropyl-1H-indol-2-yl]-3-buten-2-one and the raw material, 3-(4-fluorophenyl)-1-isopropyl-1H-indole and that the content ratio thereof (trans-4-[3-(4-fluorophenyl)-1-isopropyl-1H-indol-2-yl]-3-buten-2-one/3-(4-fluorophenyl)-1-isopropyl-1H-indole (calculated from NMR integral value)) was 1/2.7.

EXAMPLE 24

2.07 g of 1-methyl-2-phenyl-1H-indole, 1.32 g of 1,1-dimethoxy-3-butanone and 12 mL of acetic acid were mixed, then, 313 mg of 35 wt % hydrochloric acid was added into the mixture at room temperature, the added mixture was stirred for about 14 hours at the same temperature to cause a reaction. At a time point about 10 minutes after starting of stirring and reaction, blue solid precipitated to render stirring difficult. Therefore, 8 mL of acetic acid was added. After completion of the reaction, 60 mL of water was added dropwise, and the precipitated crystals were filtrated. The crystals were washed with 10 vol % methanol/water, then, dried to obtain 2.44 g of trans-4-[1-methyl-2-phenyl-1H-indol-3-yl]-3-buten-2-one (blue green solid). Yield: 89%.

$^1$H-NMR (δ/ppm, CDCl$_3$, 400 MHz)

2.24 (3H, s), 3.65 (3H, s), 6.83 (1H, d, J=16 Hz), 7.30 to 7.43 (5H, m), 7.52 to 7.59 (4H, m), 8.02 (1H, J=8 Hz)

The method of the present invention is a method of higher atom economy capable of producing an aromatic unsaturated compound which can be derived into medical and agricultural chemicals and the like without using an aromatic halide manifesting high load on environments as a raw material and without by-producing a hydrogen halide needing neutralization. Further, the method of the present invention is more advantageous also from industrial standpoint since a transition metal which is expensive and requires complicated post treatment is not used.

The invention claimed is:

1. A process for producing an aromatic unsaturated compound of the formula (4)

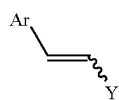
(4)

wherein Ar represents an optionally substituted aromatic group or an optionally substituted heteroaromatic group, and Y represents an electron withdrawing group, which comprises reacting (a) a compound of the formula (1)

Ar—H  (1)

wherein Ar has the same meaning as defined above with (b) a compound of the formula (2)

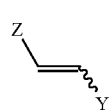
(2)

wherein Y has the same meaning as defined above, and Z represents a lower alkoxy, or a compound of the formula (3)

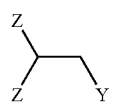
(3)

wherein Y and Z have the same meanings as defined above, in the presence of (c) an acid or a compound which generates a mineral acid by its hydrolysis, and wherein the reaction is conducted in acetic acid; and wherein Y is an alkoxycarbonyl group, an aryloxycarbonyl group, an aralkyloxycarbonyl group or a cyano group.

2. The process according to claim 1, wherein Y is an alkoxycarbonyl group having 2 to 9 carbon atoms.

3. The process according to claim 1, wherein Y is a methoxycarbonyl group.

4. The process according to claim 1, wherein Y is an aryloxycarbonyl group having 7 to 13 carbon atoms.

5. The process according to claim 1, wherein Y is an aralkyloxycarbonyl group having 8 to 14 carbon atoms.

* * * * *